United States Patent [19]

Ruf

[11] 4,083,860
[45] Apr. 11, 1978

[54] METAL COMPOUNDS OF MONOESTERS OF PHOSPHORIC ACID

[75] Inventor: Erich Ruf, Essen, Germany

[73] Assignee: Th. Goldschmidt AG, Essen, Germany

[21] Appl. No.: 670,670

[22] Filed: Mar. 26, 1976

[30] Foreign Application Priority Data

Mar. 29, 1975 Germany ............................ 2513965

[51] Int. Cl.$^2$ ............................................. C07F 7/22
[52] U.S. Cl. ..................... 260/429.7; 260/403; 260/429 R; 260/429.3; 260/429.5; 260/429.9; 260/431; 260/435 R; 260/438.1; 260/439 R; 260/446; 260/448 R; 260/448.8 A; 260/950; 260/951; 260/448 AD
[58] Field of Search ............ 260/403, 950, 951, 429.9, 260/429.7, 429 R, 448, 448.8, 429.5, 429.3, 446, 435 R, 439 R, 438.1, 431

[56] References Cited

U.S. PATENT DOCUMENTS

| | | | |
|---|---|---|---|
| 2,241,244 | 5/1941 | Conary et al. .................. | 260/950 |
| 2,346,155 | 4/1944 | Denison et al. ................. | 252/32 |
| 2,853,471 | 9/1958 | Beadell .......................... | 260/950 X |
| 3,119,853 | 1/1964 | Reetz ............................. | 260/429.9 |
| 3,944,495 | 3/1976 | Wiley et al. .................... | 260/429.9 |

*Primary Examiner*—Helen M. S. Sneed
*Attorney, Agent, or Firm*—Toren, McGeady and Stanger

[57] ABSTRACT

Compounds having the formula

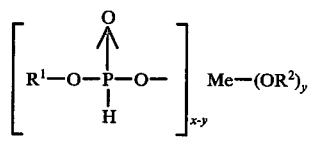

wherein
R$^1$ is the R$^3$—[O—(C$_2$H$_4$O)$_z$C$_2$H$_4$—]$_p$ group of which R$^3$ is an alkyl group with 8 to 18 carbon atoms or an alkylaryl group whose alkyl residue has at least 8 carbon atoms, or an acyl group with at least 8 carbon atoms, p has a value of 0 or 1 but must be equal to 1 when R$^3$ is an acyl group, and z = 0 or a whole number,
R$^2$ is hydrogen or the

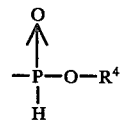

group of which R$^4$ is an alkyl residue with 1 to 4 carbon atoms,
Me is a metal or an organometallic group,
x is a whole number which corresponds to the valence of the metal or the organometallic group and
y is 0 or any whole number less than x.

These compounds are useful as corrosion inhibitors, corrosion protecting films, thickeners, and fungicides or biocides. Methods for preparing the compounds are also disclosed.

8 Claims, No Drawings

METAL COMPOUNDS OF MONOESTERS OF PHOSPHORIC ACID

BACKGROUND OF THE INVENTION

1. Field of the Invention

The invention relates to new metal compounds of monoesters of phosphoric acid as well as processes for their synthesis.

2. Description of the Prior Art

Phosphoric acid is a dibasic acid and exists in tautomeric equilibrium.

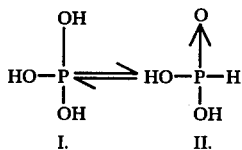

The equilibrium lies predominantly on the side of the asymmetric form II, which explains also the dibasic character of the phosphoric acid.

Ester compounds can be derived from both forms, namely, the triester of phosphoric acid and the diester of phosphoric acid. To some extent, these esters are susceptible to different reactions, as is also shown hereinafter.

The synthesis of monoesters of phosphoric acid, by the partial esterification of phosphoric acid with low molecular weight alcohols, is known, although the yields are unsatisfactory, since equilibrium mixtures of the dialkyl ester and the monoalkyl ester are produced and their separation is exceedingly difficult.

Furthermore, the hydrolysis of esters of phosphoric acid dichloride with water is known. In this reaction, it is difficult to protect the monoester compounds of phosphoric acid against further hydrolysis to phosphoric acid.

The synthesis of low-molecular-weight alcohol monoesters of phosphoric acid in the form of their sodium or ammonium salts by saponifying the corresponding diesters of phosphoric acid with alkaline or ammoniacal materials is also known.

In addition, it is known that the monobenzyl esters of phosphoric acid, if necessary, in the form of their ammonium salts, can be synthesized by reacting the dibenzyl ester of phosphoric acid with a tertiary amine, whereby a quaternary ammonium compound of the monobenzyl ester of phosphoric acid is formed which corresponds to the following formula:

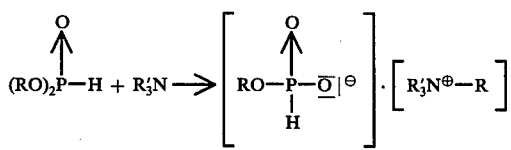

R = benzyl group
R' — low-molecular-weight alkyl

After removal of excess tertiary amine, the quaternary ammonium compound is converted with hydrochloric acid into the free monoester compound of phosphoric acid which is extracted with chloroform. The ammonium salt of the monoester compound of phosphoric acid is precipitated by passing in ammonia at 0° C.

It is furthermore known that dibenzyl esters of phosphoric acid can be partially debenzylated by partially debenzylating the diesters by reaction with sodium iodide or ammonium iodide in butanone or with lithium chloride in ethoxyethanol.

In addition, it is known that dialkyl esters of phosphoric acid, with low-molecular-weight alkyl groups, can be partially split by reaction with ammonium thiocyanate.

Another method for preparing such ester compounds utilizes the reaction of low-molecular-weight dialkyl esters of phosphoric acid in boiling toluene with the sodium salt of low-molecular-weight dialkyl esters of phosphoric acid according to the following equation:

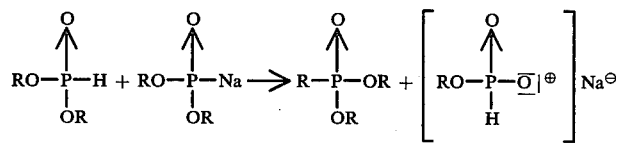

whereby, in addition to the sodium salt of monoalkyl esters of phosphoric acid with low-molecular-weight alkyl residues, dialkyl esters of alkane phosphoric acid are formed.

The synthesis of monoesters of phosphoric acid by the hydrolysis of metaphosphoric acid esters, which, in turn, are obtained by the reaction of esters of phosphoric acid dichloride with metal oxides in which the metal halides are split off is also known. This proceeds according to the following equation:

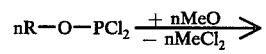

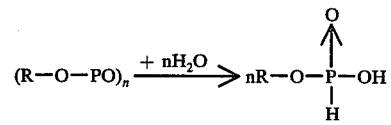

Also, low-molecular-weight monoalkyl esters of phosphoric acid can be synthesized by hydrolysing diesters of acyl phosphoric acid, such as, those obtained by reacting salicylic acid with phosphorus (III) chloride according to the following reaction equation:

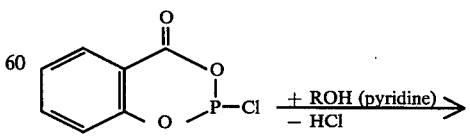

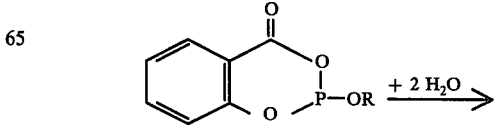

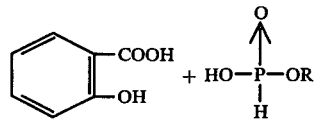

and subsequently isolating the product as the iron (III) or aniline salt by precipitation.

It is furthermore known that monoesters of phosphoric acid with low-molecular-weight alkyl residues hydrolyze rapidly in acid solutions and slowly in alkaline solutions.

SUMMARY OF THE INVENTION

The invention relates to a new type of compounds of the general formula

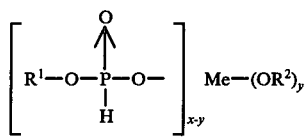

in which $R^1$ is the $R^3-[O-(C_2H_4O)-_zC_2H_4-]_p$ group of which $R^3$ is an alkyl group with 8 to 18 carbon atoms or an alkylaryl group whose alkyl residue has at least 8 carbon atoms, or an acyl group with at least 8 carbon atoms, $p$ has a value of 0 or 1 but must be equal to 1 when $R^3$ is an acyl group, and $z$ = 0 or a whole number.

$R^2$ is hydrogen or the

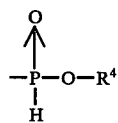

group of which $R^4$ is an alkyl residue with 1 to 4 carbon atoms,

Me is a metal or an organometallic group $x$ is a whole number which corresponds to the valence of the metal or the organometallic group and $y$ is 0 or any whole number less than $x$.

The new compounds can be synthesized especially advantageously in a two-step process, according to which initially dialkyl phosphites with low-molecular-weight alkyl residues are reacted in a nonaqueous medium and in the absence of solvents, with metal or organometallic compounds, whereupon, in a second step, the metal monoalkyl esters obtained are transesterified in order to introduce the $R^1$ substituents.

Specifically, the present process for synthesizing the new compounds is reacting, in the absence of solvents, dialkyl phosphites, whose alkyl residue has 1 to 4 carbon atoms, with anhydrous (a) metal halides, metal pseudohalides, metal sulfates or organometallic halides at a temperature that may range from 20° to 150° C; or (b) metal carboxylates or organometallic carboxylates at a temperature that may range from 70° to 150° C; or (c) metal oxides or organometallic oxides at a temperature that may range from 100° to 150° C; or (d) metal carbonates at a temperature that may range from 110° to 150° C; or (e) metal hydroxides at a temperature that may range from 90° to 150° C;

and the compounds so obtained are transesterified with compounds corresponding to the formula $R^1OH$ at elevated temperatures and preferably at a temperature in the range of 90° to 175° C, and under vacuum, if necessary.

DESCRIPTION OF THE PREFERRED EMBODIMENT

According to this definition, the $R^3$ group is a straight chained or branched alkyl residue with 8 to 18 carbon atoms, e.g., the nonyl, dodecyl, i-tridecyl, hexadecyl or octadecyl residue. Furthermore, the $R^3$ group can be an alkylaryl group whose alkyl residue has at least 8 carbon atoms. Such groups are, for example, octylphenyl, nonylphenyl, dodecylphenyl, and the like. The $R^3$ group can also be joined by an oxyethylene or a polyoxyethylene bridge to the oxygen which is connected to the phosphorus.

The $R^3$ group can also be an acyl group with at least 8 carbon atoms. However, this acyl group must in every case be joined by an oxyethylene or a polyoxyethylene bridge to the oxygen which is connected to the phosphorus.

Me is a metal. Especially preferred are the metals of the first to the fifth main group of the periodic table, as well as the sub-groups, particularly, the alkali metals, alkaline earth metals, Al, Si, Ti, Zr, Sn, Sb, Pb, Fe, Co, Ni, Cu, Zn, Cd, Hg, and rare earth metals, including Y.

The organometallic groups contain especially tin and silicon as metals.

Examples of such groups are dimethyltin, tributyltin or trimethylsilyl.

$x$ corresponds to the valence number of the metal or the organometallic group, which is available for combining with the surface active phosphoric acid ester groups.

$y$ is equal to 0 or any whole number less than $x$. Accordingly, if $x = 3$, $y$ can have the values 0, 1 or 3.

Especially suitable as metal halides are alkali halides, alkaline earth halides, zinc halides, cadmium halides, tin (II) halides and aluminum halide compounds. Alkyltin halides and alkylsilyl halides are preferred as organometallic halides.

As used herein, the term pseudometal halides, which is a well known term of art, means those metal compounds which behave like halides in their reactivity. Metal cyanides are pseudohalides of this type.

If the metal halide used reacts appreciably at a temperature below 100° C, the reaction can be carried out with all of the reactants in the reactor, since the transesterification of the low-molecular-weight esters with compounds corresponding to the formula $R^1OH$ only commences at a temperature of 100° C or higher.

However, if the reaction temperature of the metal halides with the low-molecular-weight dialkyl phosphite on the one hand overlaps with that of the transesterification of the resulting low-molecular-weight metal phosphoric acid ester with compounds corresponding to the formula $R^1OH$ on the other, the two reaction steps should be carried out separately or in sequence.

The metal halides which may be used for the first reaction step, must be anhydrous since in the presence of water, even in the form of water of crystallization, partial hydrolysis occurs, especially at the reaction temperatures, with liberation of hydrogen chloride and consequently, lesser yields are obtained with partial formation of purely inorganic metal phosphites.

In the reaction of low-molecular-weight dialkyl phosphites with metal halides, which proceeds quantitatively in the absence of solvents, the reactivity of the various metal halides is different. For example, lithium chloride reacts exothermally with dimethyl phosphite readily at room temperature, whereby a vigorous evolution of methyl chloride occurs from about 50° upwards. Calcium chloride also reacts exothermally with dimethyl phosphite, however, the evolution of methyl chloride commences at about 70° C. Potassium cyanide reacts exothermally with dimethyl phosphite at temperatures above 70° C, and the temperature of the reaction mixture generally rises to above 100° C so that acetonitrile can be distilled off. Lead chloride reacts with dimethyl phosphite at temperatures of about 100° C, while barium chloride and zinc chloride react at temperatures at or above 115° C, sodium chloride from about above 120° C and potassium chloride from about above 135° C.

When the two reaction steps are carried out separately or sequentially, i.e., the reaction of low-molecular-weight alkyl phosphites with metal halides or organometallic halides on the one hand and the transesterification of the resultant low-molecular-weight metal phosphoric acid monoesters with compounds corresponding to the formula R$^1$OH on the other, the dialkyl phosphites employed should be used in excess in the first reaction step, since the resulting low-molecular-weight metal phosphoric acid monoesters can be stirred and mixed more readily in an excess of dialkyl phosphite. Also, the excess ensures that only one alkyl group per molecule of dialkyl phosphite reacts to form alkyl halide.

In the reaction, attention must be paid to the temperature range, since otherwise partial formation of purely inorganic metal phosphites is possible. These compounds are, of course, no longer capable of transesterfication.

Just as metal halides of pseudo-metal halides, also anhydrous metal sulfates, such as, for example, sodium sulfate and anhydrous metal sulfides, for example, sodium sulfide, react with low-molecular-weight dialkyl phosphites such that in addition to the low-molecular-weight metal phosphite compounds, dialkyl sulfate and some alcohol are formed in the case of sodium sulfate and dialkyl thioether. With sodium sulfide, alkyl mercaptan as well as dialkyl disulfide are also formed.

In the process of the present invention, the first reaction step can also be carried out using metal carboxylates, such as, for example, sodium formate, sodium acetate, sodium propionate, calcium formate, calcium acetate, tin (II) formate, zinc formate, cadmium formate, antimony formate, and aluminum acetate or with organometallic carboxylates, such as, for example, tributyltin acetate in a manner analogous to those with the metal halides.

These reactions also proceed practically to completion in the absence of solvents, and the reaction temperatures are generally only insignificantly higher than those for metal halides, and are between 70° and 150° C. The corresponding alkyl esters of the carboxylic acids are formed in addition to the metal phosphoric acid monoesters with low-molecular-weight alkyl residues.

In another embodiment of the process of the present invention, dialkyl phosphites with low-molecular-weight alkyl residues are reacted with metal oxides or organometallic oxides, such as, for example, tributyltin oxide. These reactions also proceed practically quantitatively in the absence of solvents with low-molecular-weight alcohols and/or ether being split off. The reaction temperatures lie preferably between about 100° and 150° C.

A different embodiment of the present process comprises the essentially quantitative conversion of phosphites with anhydrous metal carbonates, in the absence of solvents, to metal phosphoric acid monoester compounds with low-molecular-weight alkyl residues, in a manner analogous to that with metal oxides, whereby carbon dioxide is also liberated quantitatively. The reaction temperatures lie especially between about 110° and 150° C.

A further embodiment comprises the practically quantitative synthesis of the metal phosphoric acid monoester compounds with low-molecular-weight alkyl residues, in the absence of solvents, by reacting low-molecular-weight dialkyl phosphites with anhydrous metal hydroxides, whereby at the same time, the corresponding low-molecular-weight alcohol is formed.

The compounds, synthesized according to the various methods described, can be transesterified in a second step with compounds corresponding to formula R$^1$HO at elevated temperatures and especially at temperatures in the range of 90° to 175° C. These transesterification reactions proceed at different rates.

Thus, whereas transesterifications with fatty alcohols with at least 8 carbon atoms proceed relatively quickly, particularly between 80° and 175° C, transesterifications with alkoxylated alkylphenols with at least 8 carbon atoms in the alkyl residue, alkoxylated fatty alcohols with at least 8 carbon atoms in the fatty alkyl residue, alkoxylated products of fatty acids with at least 8 carbon atoms in the fatty acid residue, and alkyl phenols with at least 8 carbon atoms in the alkyl residue, proceed more slowly. In these cases, it is recommended that the transesterifications be carried out under a vacuum of about 5 to 100 torr. The reaction temperatures for these reactions lie mainly between 100° and 175° C.

The course of the inventive process is somewhat surprising since low-molecular-weight triesters of phosphoric acid, such as, for example, trimethyl phosphite or triethyl phosphite do not react, under analogous conditions, to any appreciable extent with metal halides. Moreover, they practically do not react at all with metal carboxylates, metal oxides or with metal carbonates to form the corresponding esters of metal phosphoric acid.

Compounds of the invention with divalent or multivalent metal cations can also be obtained by dissolving or dispersing the corresponding alkali compounds in water and reacting these solutions or dispersions, hot if possible, with metal salts of divalent or multivalent metal cations. Because of their relative insolubility in water, the metal phosphoric acid ester compounds with divalent or multivalent metal cations which are formed, are precipitated and isolated and dried according to known methods.

Compounds produced according to the invention have different physical and chemical properties depending on the metal used, the type of R$^1$ and R$^2$ residues and the value of the indexes $x$ and $y$. They can therefore be used in different fields of application.

Alkali metal phosphite esters in which $R^1$ is an alkyl group with up to about 13 carbon atoms or in which $R^1$ is a nonylphenyl residue, are at least partially soluble in distilled water. The solubility in water decreases for residues with longer alkyl chains. The compounds however remain readily dispersible in water. Compounds with divalent or multivalent metal and alkyl residues of longer chain length are frequently soluble in mineral oil and in addition, also frequently soluble in different organic solvents, such as, for example, cyclohexanol, cyclohexanone, chloroform, xylene, white spirits and butyl acetate.

The possibilities for using these compounds are correspondingly variable. For example, sodium nonylphenyl phosphite or sodium oleyl phosphite or the analogous potassium or lithium compounds can be used as valuable corrosion inhibitors in aqueous systems. Since the compounds just named are largely soluble in distilled water or readily dispersible in tap water, they can be used directly for inhibiting corrosion of aqueous systems.

In addition, the compounds of the invention can be used to advantage as active materials for corrosion protection oils for temporary corrosion protection. Especially suitable for this purpose are mixtures of alkali nonylphenyl phosphites or alkali oleyl phosphite with calcium di-(nonylphenylpolyoxyethylene phosphite) or calcium di-(oleyl phosphite), if necessary, in mixture with other materials.

Just as metal stearates on the one hand and triesters of phosphoric acid on the other are used as additives for plastics, certain metal di-(lauryl phosphites) or metal di-(stearyl phosphites), such as, for example, the corresponding calcium, zinc and tin(II) compounds are also suitable for this purpose.

Compounds in which $R^3$ is an ethoxylated fatty acid residue, are water or oil soluble, depending on the number of carbon atoms in the fatty acid residue and the degree of ethoxylation, and are suitable in both systems as active materials for temporary rust protection.

Aluminum oleyl phosphite di-(methylphosphite) compounds, which dissolve in xylene after prolonged heating, have a marked thickening effect and can therefore be used to advantage for adjusting consistency, i.e., as thickeners.

Some tributyltin phosphite compounds, such as, for example, tributyltin methyl phosphite or tributyltin ethyl phosphite have fungicidal or biocidal properties.

The synthesis of the inventive compounds shall be illustrated in greater detail by means of the following examples:

EXAMPLE 1

In a four-neck round-bottom flask, equipped with a stirrer, thermometer, reflux condenser and standard taper stopper and connected by means of a gas offtake tube, attached to the condenser, with a cold trap which is cooled to about $-65°$ C with a cooling mixture, 58.4 g sodium chloride and 121 g dimethyl phosphite are heated with stirring for about 1 hour at 100° to 200° C. The reaction commences at about 100° C, methyl chloride being split off. Subsequently, the reaction mixture is further heated for about 6 hours with stirring at about 130° to 140° C. After a practically quantitative cleavage of methyl chloride, the excess of dimethyl phosphite is distilled off under vacuum (about 5 mm Hg). 115 g sodium methyl phosphite are obtained.

After cooling, the sodium methyl phosphite obtained is reacted at about 50° C with 266 g of oleyl alcohol. After exchanging the reflux condenser for a stillhead, condenser and cooled distillation receiver, the reaction mixture is heated with stirring to about 150° C with methanol being distilled off.

After 6 hours of heating with a vacuum (100 – 5 mm Hg) applied for the last two hours, and excess dimethyl phosphite being distilled off, the reaction is practically complete. 340 g sodium oleyl phosphite are obtained. The product has a melting point of about 90° C. The product dissolves in xylene, and in butyl acetate with heating, to form an almost clear solution. Sodium oleyl phosphite is water dispersable.

EXAMPLE 2 (Dropwise Addition)

37 g anhydrous calcium chloride and 68.8 g of lauryl alcohol are added to a glass apparatus as described in Example 1. 75.3 g dimethyl phosphite are added by means of a dropping funnel.

The reaction mixture is heated with stirring at about 70° to 80° C, whereby methyl chloride is split off at about 72° C. After heating for 4½ hours with stirring, the evolution of methyl chloride has largely ended. Now 68.8 g lauryl alcohol are once again added. The reaction mixture is cooled to about 40° C. The reflux condenser with the gas offtake tube is exchanged for a stillhead, condenser and cooled distillate receiver and the reaction mixture is then heated with stirring to about 98° C, whereupon methanol begins to distill off.

The reaction mixture is then heated further with stirring for 1 hour at about 150° C and thereafter for about another 1.5 hours at 150° C under a vacuum of about 100 to 5 mm Hg to distill off the excess lauryl alcohol. After a total reaction time of 2.5 hours at 150° C, 191 g calcium-di-(lauryl phosphite) are obtained.

The product has a melting point of about 90° C. Calcium di-(lauryl phosphite) is soluble in hot xylene, white spirits, butanol and butyl acetate.

EXAMPLE 3

In a 250 ml four-neck round-bottom flask, equipped with thermometer, stirrer, standard taper glass stopper and a small Vigreux column with stillhead, condenser, cooled distillate receiver and cold trap (cooled to $-65°$ C with a cooling mixture), 83 g potassium iodide and 60.5 g dimethyl phosphite are heated with stirring to about 85° C. The reaction commences at about 70° C and methyl iodide is distilled off. The reaction mixture is heated for about 2 hours to a temperature not exceeding 90° C. Subsequently, the reaction mixture is heated for a further two hours under vacuum (about 20 mm Hg) to a temperature not exceeding 105° C. After distilling off the residual amount of methyl iodide, excess dimethyl phosphite is distilled off and 67.3 g potassium methyl phosphite are obtained.

In a 250 ml four-neck flask equipped with a thermometer, stirer, standard taper glass stopper, still head with condenser and including a cooled distillate receiver and cold trap, 67.3 g potassium methyl phosphate are heated with 102.2 g lauryl alcohol for about 3½ hours at 140° to 145° C.

Methanol is distilled off and, subsequently, the reaction mixture is heated with stirring for about an additional 3 hours under vacuum, ca. 20 mm Hg, at 150° C. 156 g potassium lauryl phosphite are obtained.

The product has a softening point of about 140° C. Potassium lauryl phosphite is soluble in hot cyclohexanone. Furthermore, it is partly soluble in hot xylene, white spirits and ethanol, forming a cloudy solution. The product is soluble in hot distilled water. The aqueous solution is neutral.

EXAMPLE 4

In a 500 ml four-neck round-bottom flask equipped with a strirrer, thermometer, standard taper glass stopper, Vigreux column with stillhead, condenser, cooled distillate receiver and cold trap (cooled with cooling mixture to −65° C), 32.55 g of potassium cyanide and 110 g of dimethyl phosphite are slowly heated with stirring to about 70° C. a vigorous reaction commences and the temperature of the reaction mixture increases to 130° C. At the same time, acetonitrile is distilled off.

After heating for 2 hours with stirring at 130° C, the reaction mixture is heated for about an additional two hours under vacuum (100 – 5 mm Hg) at 130° – 140° C, in order to distill off the residual acetonitrile as well as the excess dimethyl phosphite. 63 g potassium methyl phosphite are obtained.

In a 500 ml round-bottom four-neck flask (stirrer, thermometer, standard taper glass stopper, stillhead with condenser and cooled distillate receiver and cold trap), 63 g potassium of methyl phosphite are heated with stirring with 107 g of oleyl alcohol for about 6 hours at about 160° C with a vacuum of about 25 mm Hg being applied for the last 2 hours. Methanol is distilled off and 157.3 g potassium oleyl phosphite are obtained.

The product has a melting point of about 75° C. The product forms a clear solution in xylene and is soluble, with slight cloudiness, in hot butyl acetate, cyclohexanone, white spirits and ethylene chloride. The product can be dispersed in distilled water.

EXAMPLE 5

In a 500 ml four-neck round-bottom flask equipped with a stirrer, thermometer, standard taper glass stopper, reflux condenser with gas takeoff tube and cooled cold trap, 73.2 g of dimethyltin dichloride and 77 g of dimethyl phosphite are heated with stirring to about 120° to 130° C. At about 120° C, methyl chloride commences to be split off. After a reaction time of 1½ hours, the reflux condenser with gas takeoff tube is exchanged for a stillhead with a distillate receiver. Subsequently, the reaction mixture is heated with stirring for 1 hour at 100° to 120° C under a vacuum of about 5 mm Hg, in order to distill off excess dimethyl phosphite. 111.8 g dimethyltin phosphite are obtained.

The amount of dimethyltin phosphite obtained is heated in the same apparatus with stirring with 137.4 g of lauryl alcohol at about 160° C for 3 hours, a vacuum of 100 – 25 mm Hg being applied for the last hour. Methanol is split off from about 115° C upwards. 227 g of dimethyltin di-(lauryl phosphite) are obtained.

The softening point of dimethyltin di-(lauryl phosphite) is about 50° C. The product is soluble in xylene, butyl acetate, cyclohexanol, cyclohexanone, white spirits and ethylene chloride.

EXAMPLE 6

In a 1000 ml four-neck round-bottom flask (thermometer, stirrer, standard taper glass stopper, stillhead with condenser, cooled distillate receiver and cold trap), 68 g sodium formate and 115 g dimethyl phosphite are heated with stirring for about 3 hours at about 100° to 115° C. The reaction commences at about 100° C, methyl formate being split off. The reaction mixture is heated with stirring for approximately a further hour under vacuum (5 mm Hg) to distill off the residual amount of methyl formate as well as the excess dimethyl phosphite. 118 g sodium methyl phosphite are obtained.

The sodium methyl phosphite obtained (118 g) is heated with stirring with 270 g stearyl alcohol in the same glass apparatus at about 150° C, methanol being distilled off. After heating for 4 hours at 150° C and an additional hour under vacuum at this temperature, 360 g of sodium stearyl phosphite are obtained.

Sodium stearyl phosphite has a melting point of about 130° C. The product is soluble in warm xylene, butyl acetate (the solution is almost clear) and partially soluble in warm white spirits. The product has thickening properties and is dispersible in water.

EXAMPLE 7

In a 500 ml four-neck round-bottom flask having a thermometer, stirrer, standard taper glass stopper, stillhead with condenser, cooled distillate receiver and cold trap, 116.4 g of tributyltin acetate and 92 g of diethyl phosphite are heated with stirring to about 150° with ethyl acetate being distilled off. After a reaction time of 6 hours, of which one hour is under vacuum, ca. 5 mm Hg, the excess dimethyl phosphite is distilled off and 134 g of tributyltin ethyl phosphite are obtained.

In a 500 ml four-neck round-bottom flask equipped with a stirrer, thermometer, standard taper glass stopper, stillhead with condenser, cooled distillate receiver and cold trap, 133 g of tributyltin ethyl phosphite and 68.7 g of lauryl alcohol are heated with stirring for about 5 hours at 140° C, a vacuum of about 30 – 5 mm Hg being applied for 1 hour. Ethanol is initially distilled off and then the excess lauryl alcohol is distilled. 178 g tributyltin lauryl phosphite are obtained.

Tributyltin lauryl phosphite is highly viscous at room temperature. The product is soluble in xylene and in hot cyclohexanone and ethylene chloride.

EXAMPLE 8

In a glass apparatus as described in Example 1, 14 g of calcium oxide and 110 g of dimethyl phosphite are heated with stirring for about 7 hours at 130° to 140° C. The reaction commences at about 130° C. Initially methanol is split off and later dimethyl ether is split off. Subsequently, the reaction mixture is heated for 2 hours under a vacuum of 20 to 5 mm Hg at 130° to 140° C, whereby excess dimethyl phosphite is also distilled off. After a reaction of 9 hours, 54 g of reaction product are obtained.

It is assumed that the product is a mixture of calcium methyl phosphite, calcium-di-(methyl phosphite) and calcium monomethyl pyrophosphite.

54 g of the above-mentioned reaction mixture are heated for 3 hours with stirring with 150 g of oleyl alcohol at a temperature of about 155° C and subsequently for a further 1½ hours at this temperature under a vacuum of 20 to 5 mm Hg. 201 g of oleyl ester of the above-mentioned calcium phosphite or calcium pyrophosphite compounds are obtained, in which the respective methyl groups are replaced by oleyl groups.

The reaction product melts at about 50° C and is soluble in mineral oil.

EXAMPLE 9

In a glass apparatus as described in Example 1, 25.03 g of calcium carbonate and 110 g of dimethyl phosphite are heated with stirring for about 8 hours at 145° to 150° C. The reaction commences at about 145° C, carbon dioxide and methanol being split off. Furthermore, dimethyl ether is split off during the reaction. The reaction mixture is then stirred for a further two hours at this temperature under a vacuum of 20 to 5 mm Hg, whereby excess dimethyl phosphite is distilled off. 75.5 g of reaction product are obtained.

It is assumed that, analogously to the reaction of Example 8, a mixture of calcium methyl phosphite, calcium-di-(methyl phosphite) and calcium monomethyl pyrophosphite is also obtained here.

The reaction mixture obtained is heated with 220 g oleyl alcohol for 4½ hours at 155° to 160° C, whereby methanol is distilled off. The reaction mixture is then stirred under a vacuum of 20 to 5 mm Hg for a further 2 hours at this temperature. 276 g oleyl esters of the above-mentioned calcium phosphite and calcium pyrophosphite compounds are obtained.

The reaction product is soluble in mineral oil. The melting point of the reaction product is about 50° C.

EXAMPLE 10

In a 250 ml four-neck round-bottom flask with stirrer, thermometer, standard taper glass stopper, stillhead including condenser, cooled distillate receiver and cold trap, 54 g anhydrous basic aluminum hydroxide diacetate are heated with 110g dimethyl phosphite with stirring at 110° C. Methyl acetate and methanol are split off since both acetate groups as well as the OH group react practically quantitatively with dimethyl phosphite. After a reaction time of two hours, the reaction mass, which is solid, is cooled, comminuted, heated with stirring under a vacuum to 90° C and subsequently for 1½ hours under vacuum at 150° C. 103 g aluminum trimethyl phosphite are obtained.

73 g aluminum trimethyl phosphite are heated in the same glass apparatus with 188 g oleyl alcohol with stirring for about 9 hours at 165° C. Altogether, only one methyl group of aluminum trimethyl phosphite is transesterified, so that 251 g of a mixture, consisting of the oleyl phosphate of aluminum di(methyl phosphite) and oleyl alcohol, result.

After several hours of heating, this reaction mixture dissolves in xylene with a great increase in viscosity.

EXAMPLE 11

In a 500 ml four-necked round-bottom flask, as described in Example 1, 37.05 g anhydrous calcium hydroxide and 220 g dimethyl phosphite are heated with stirring at about 140° C. The reaction commences at about 115° C, methanol being split off. After 2 hours of heating at 140° C, the reaction mixture is heated a further 2 hours under a vacuum of 100 – 5 mm Hg, with stirring at 100° to 130° C. Since the reaction mixture foams strongly, the vacuum must be applied slowly. 125 g of calcium-di-(methyl phosphite) are obtained. The product contains small amounts of dimethyl phosphite.

67 g of the reaction product (calcium di-(methyl phosphite)) are heated with stirring with 155 g of oleyl alcohol in a 500 ml four-neck round-bottom flask (stirrer, thermometer, standard taper glass stopper, stillhead with condenser, cooled distillate receiver and cold trap) for 4 hours at about 140° to 160° C and 1 hour under a vacuum of about 5 mm Hg at 155° C. 254.3 g of calcium-di-(oleyl phosphite) are obtained.

The product is soluble in xylene and chloroform and extensively soluble in hot mineral oil, white spirits, ethyl acetate, cyclohexanol and cyclohexanone. The product has a melting point of about 70° C.

EXAMPLE 12

In a 500 ml four-neck round-bottom flask, as described in Example 1, 148.85 g of tributyltin oxide and 110 g dimethyl phosphite are heated with stirring to about 120° C. The reaction mixture is kept at this temperature for about 2 hours, dimethyl ether being split off. The reaction mixture is then heated with stirring under a vacuum of 20 to 5 mm Hg at 145° C, until the excess dimethyl phosphite has been distilled off. 193.3 g of tributyltin methyl phosphite are obtained. 128.5 g of tributyltin methyl phosphite and 68.7 g of lauryl alcohol are heated with stirring in a 500 ml four-neck round-bottom flask equipped with a stirrer, thermometer, standard taper glass stopper, stillhead with condenser, cooled distillate receiver and cold trap at 140° C for 5 hours, for one hour of which a vacuum (30 – 5 mm HG) is applied. Methanol is distilled off. 178 g tributyltin lauryl phosphite are obtained.

The product is very viscous at room temperature. The product is soluble in hot xylene, cyclohexanol, cyclohexanone and ethylene chloride.

EXAMPLE 13

In a 500 ml four-neck round-bottom flask, having a stirrer, thermometer, standard taper glass stopper, stillhead with cooled distillate receiver and cold trap, 59 g of sodium methyl phosphite, synthesized as in Example 6, and 197.5 g of tetraethyleneglycol-mon-(nonylphenyl ether) are heated for 16 hours with stirring at about 140° to 150° C. A vacuum of 120 –130 mm Hg is applied for about half of the reaction time when methanol is distilled off. 240 g of sodium nonylphenylpoly(oxyethylene)-phosphite are obtained.

The product is semifluid at room temperature. Sodium nonylphenyl-poly-(oxyethylen)-phosphite is soluble in xylene and water. The pH of the aqueous solution is about 7.

EXAMPLE 14

59 g of sodium methyl phosphite are synthesized according to the procedure in Example 6. This amount of soldium methyl phosphite and 55 g of nonylphenol are heated with stirring in a 500 ml four-neck round-bottom flask equipped with a stirrer, thermometer, standard taper glass stopper, stillhead with cooled distillate receiver and cold trap at about 160°C under a vacuum of 100 mm Hg, methanol being distilled off. After a reaction time of one half hour, an additional 57 g of nonyl phenol are added to the reaction mixture. After a reaction time of 7¼ hours at 160° C under a vacuum of about 100 mm Hg, the vacuum is increased to about 5 mm Hg during the last 1¾ hours. 143 g of sodium nonylphenyl phosphite are obtained.

Sodium nonylphenyl phosphite has a softening point of about 150° C. The product forms a slightly cloudy solution in water and a colloidal solution is hot butyl acetate and in ethanol.

EXAMPLE 15

In a 800 ml beaker, 20 g of sodium lauryl phosphite and 400 ml distilled water are brought to a temperature of about 90° C with stirring. An almost clear solution is obtained. 8 g of calcium chloride, dissolved in 50 ml water and also heated to 90° C, were added with stirring to this sodium lauryl phosphite solution. Calcium-di- (lauryl phosphite) is formed immediately which floats initially but sinks to the bottom on cooling. The pH value after precipitation is about 6 to 7.

After cooling, the precipitate is decanted several times with warm water at about 45° C, until the chloride test is negative.

88 g of moist calcium-di-(lauryl phosphite) are obtained from which the water is removed subsequently with xylene. After distillative removal of xylene and water, 19.9 g of calcium-di-(lauryl phosphite) are obtained.

EXAMPLE 16

In a 500 ml four-neck round-bottom flask with a stirrer, thermometer, standard taper glass stopper, stillhead with cooled distillate receiver and cold trap, 39.3 g of sodium methyl phosphite are synthesized according to the procedure given in Example 6, and 201 g of anhydrous decaethyleneglycolmonethyl ether are heated for about 17 hours with stirring at 160° C under a vacuum of about 80 mm Hg with methanol being distilled off. When the reaction is completed, 229.5 g of sodium oleyl-poly(oxyethylene)-phosphite are obtained.

The product is liquid at room temperature and colored a light brown. The product is soluble in water, forming a slightly cloudy solution.

EXAMPLE 17

In a 500 ml four-neck round-bottom flask equipped with a stirrer, thermometer, standard taper glass stopper, stillhead with cooled distillate receiver and cold trap, 17.7 g of sodium methyl phosphite and 231 g of anhydrous poly-(oxyethylene)-stearate corresponding to the formula

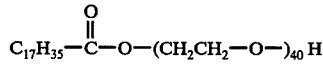

are heated with stirring for about 17 hours at about 160° C under a vacuum of about 80 mm Hg with methanol being split off. When the reaction is completed, 234 g of sodium stearoyl-poly(oxyethylene)-phosphite are obtained.

The product has a softening point of ca. 45° C and is soluble in water.

EXAMPLE 18

In a 500 ml four-neck round-bottom flask, equipped with a stirrer, thermometer, standard taper glass stopper, stillhead with cooled distillate receiver and cold trap, 118 g of sodium methyl phosphite and 226 g of lauryl alcohol are heated for 5 hours up to about 160° C with a vacuum of about 5 mm Hg being applied during the last half hour. In this last half hour, excess lauryl alcohol is distilled off. 304 g of reaction product (sodium lauryl phosphite) with 4% of free lauryl alcohols are obtained.

The reaction product has a melting point of about 120° C. Sodium lauryl phosphite is extensively soluble in hot distilled water, xylene, white spirits and butyl acetate. Sodium lauryl phosphite has thickening properties.

What is claimed is:

1. Compound corresponding to the formula

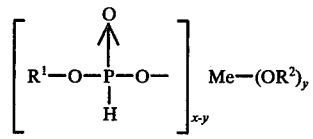

in which
R¹ is the R³—[O—(C₂H₄O)₂C₂H₄—]$_p$ group of which
R³ is an alkyl group with 8 to 18 carbon atoms or an akylaryl group whose alkyl residue has at least 8 carbon atoms,
p has a value of 0 or 1, and
z = 0 or a whole number,
R² is hydrogen or the

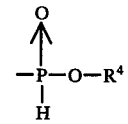

group of which
R⁴ is an alkyl residue with 1 to 4 carbon atoms,
Me is a metal selected from the group consisting of alkaline earth, alkali and rare earth metals,
x is a whole number which corresponds to the valence of the metal or the organometallic group and
y is 0 or any whole number less than x.

2. The compound of claim 1 wherein the metal is alkaline earth or alkali.

3. Compound corresponding to the formula

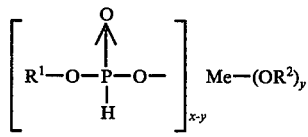

in which
R¹ is the R³—[O-(C₂—H₄O)₂C₂H₄—]$_p$ group of which
R³ is an alkyl group with 8 to 18 carbon atoms or an alkylaryl group whose alkyl residue has at least 8 carbon atoms,
p has a value of 0 or 1, and
z = 0 or a whole number,
R² is hydrogen or the

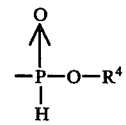

group of which
R⁴ is an alkyl residue with 1 to 4 carbon atoms,
Me is a metal selected from the group consisting of Al, Si, Ti, Zr, Sn, Sb, Pb, Fe, Co, Ni, Cu, Zn, Cd, Hg and Y,
x is a whole number which corresponds to the valence of the metal or the organometallic group and
y is 0 or any whole number less than x.

4. The compound of claim 3 wherein the metal is Al, Pb, Fe, Cu, Zn, or Cd.

5. Compound corresponding to the formula

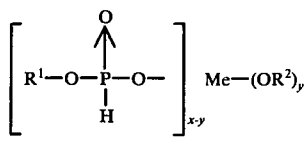

in which

R$^1$ is the R$^3$—[O-(C$_2$H$_4$O)$_z$C$_2$H$_4$—]$_p$ group of which

R$^3$ is an alkyl group with 8 to 18 carbon atoms or an alkylaryl group whose alkyl residue has at least 8 carbon atoms, p has a value of 0 or 1, and z = 0 or a whole number, R$^2$ is hydrogen or the

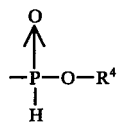

group of which

R$^4$ is an alkyl residue with 1 to 4 carbon atoms,

Me is an organometallic group containing Sn or Si as the metal, x is a whole number which corresponds to the valence of the metal or the organometallic group and y is 0 or any whole number less than x.

6. The compound of claim 5 wherein Me is dimethyltin, tributyltin or trimethylsilyl.

7. The compound of claim 1 wherein R$^3$ is alkylaryl and the aryl portion is phenyl.

8. The compound of claim 1 wherein Z is in the range from 0 to about 40.

* * * * *